United States Patent
Zheng et al.

(10) Patent No.: US 7,117,027 B2
(45) Date of Patent: Oct. 3, 2006

(54) METHOD FOR ESTABLISHING A THREE-DIMENSIONAL REPRESENTATION OF A BONE FROM IMAGE DATA

(75) Inventors: Guoyan Zheng, Bern (CN); Lutz-Peter Nolte, Thun (CN)

(73) Assignee: Synthes (USA), Paoli, PA (US)

( * ) Notice: Subject to any disclaimer, the term of this patent is extended or adjusted under 35 U.S.C. 154(b) by 68 days.

(21) Appl. No.: 10/629,589

(22) Filed: Jul. 30, 2003

(65) Prior Publication Data
US 2004/0111024 A1  Jun. 10, 2004

Related U.S. Application Data

(63) Continuation of application No. PCT/CH01/00086, filed on Feb. 7, 2001.

(51) Int. Cl.
*A61B 5/05* (2006.01)

(52) U.S. Cl. .............. 600/426; 600/410; 600/415; 600/424; 600/425; 600/426; 600/427; 600/443; 378/4; 378/5; 378/8; 378/9; 378/92; 378/196

(58) Field of Classification Search .......... 600/427, 600/426, 410, 415, 424, 425, 443, 407; 378/4, 378/5, 8, 9, 92, 196
See application file for complete search history.

(56) References Cited

U.S. PATENT DOCUMENTS

| | | | | |
|---|---|---|---|---|
| 5,229,935 | A | 7/1993 | Yamagishi et al. | 364/413.22 |
| 5,383,454 | A | 1/1995 | Bucholz | 128/653.1 |
| 5,682,886 | A | 11/1997 | Delp et al. | 128/653.1 |
| 5,715,836 | A | 2/1998 | Kliegis et al. | 128/898 |
| 5,871,018 | A | 2/1999 | Delp et al. | 128/898 |
| 6,560,476 | B1 * | 5/2003 | Pelletier et al. | 600/410 |
| 6,711,432 | B1 * | 3/2004 | Krause et al. | 600/427 |
| 6,816,564 | B1 * | 11/2004 | Charles et al. | 378/5 |
| 2004/0028181 | A1 * | 2/2004 | Charles Jr. et al. | 378/92 |

FOREIGN PATENT DOCUMENTS

| | | |
|---|---|---|
| EP | 0359773 | 2/1993 |
| EP | 1004272 | 5/2000 |

OTHER PUBLICATIONS

R. Hofstetter et al., "Computer-Assisted Fluoroscopy-Based Reduction of Femoral Fractures and Antetorsion Correction," *Computer Aided Surgery*, 5:311-325, 2000.

Z. Boljevic et al., "Computer-Assisted Three-Dimensional Modelling for Definition and Correction of Deformities in Orthopaedic Surgery," 1993 Proc. Int. Conf. Information Technology Interfaces, Jun. 1993, pp. 357-364.

S. Lavallee et al., "Matching of Medical Images for Computed and Robot Assisted Surgery," *Computed Tomography* 12:4-1, pp. 39-40, Oct. 1991.

* cited by examiner

*Primary Examiner*—Brian L. Casler
*Assistant Examiner*—Baisakhi Roy
(74) *Attorney, Agent, or Firm*—Jones Day

(57) ABSTRACT

A system and method for preparing a virtual three-dimensional representation of a first portion of a bone. The method may comprise obtaining, from a first orientation with respect to the first portion of the bone, first image data of the first portion of the bone and obtaining, from a second, different orientation with respect to the first portion of the bone, second image data of the first portion of the bone. A three-dimensional (3D) virtual representation of the first portion of the bone may be generated. The 3D virtual representation of the first portion of the bone may be displayed. The displayed 3D virtual representation may have an orientation, determined using at least the difference between the first and second orientations from which the first and second image data were obtained.

30 Claims, 4 Drawing Sheets

METHOD FOR ESTABLISHING A THREE-DIMENSIONAL REPRESENTATION OF A BONE FROM IMAGE DATA

RELATED APPLICATIONS

The present application is a continuation of international application no. PCT/CH01/00086, filed 7 Feb. 2001, which application is incorporated herein by reference.

FIELD OF THE INVENTION

The present invention relates to a method for preparing a three-dimensional representation of a bone or portion thereof from imaging data.

BACKGROUND OF THE INVENTION

Computer assisted surgery systems (CAS systems) or image guided surgery systems that are provided with a computer and a position measurement device in order to measure the position of surgical instruments, devices and a body portion of the patient are often used to perform minimally invasive surgery. Computer assisted surgery systems (CAS-systems) are disclosed e.g. in EP 0 359 773 to Schlöndorff, U.S. Pat. No. 5,383,454 to Buchholz and in U.S. Pat. No. 5,682,886 Delp. CAS systems may comprise a memory means to store medical images such as e.g. X-rays, computertomographs or MR images (magnetic resonance images). Thereby the medical images may be gathered pre-operatively or intraoperatively.

Computer assisted orthopaedic surgery systems include a) CT based systems, which may use a preoperative CT (Computertomogram) of a bone or bone fragment to establish a three-dimensional anatomical model that is referenced with the intraoperative respective bone or bone fragment through landmark based or surface based registration or matching; b) CT based and fluoroscopy systems, which use the same method as CT based systems to establish a three-dimensional anatomical model, whereby the preoperative CT of a bone or bone fragment is registered or matched to the intraoperative respective bone or bone fragment through using a surface model of the bone or bone fragment and its projections in the planes of the fluoroscopic images; and c) fluoroscopy based systems, which use calibrated fluoroscopes to generate undistorted images of a bone or bone fragment and virtual geometric representations of the projection of surgical tools.

A method of generating tomographic images of a body using penetrating radiation is known from EP 1004272 to Lin. This known method comprises the steps of a) cycling the radiation source among a plurality of positions relative to the region of interest of the body such that radiation from the radiation source passing through each of a plurality of focal planes, which are parallel to the detector plane and within the region of interest, impinge upon the detector plane superimposed and offset from each other; b) shifting the electronic views for a first selected focal plane, such that the radiation which passes through each incremental element of the first selected focal plane contributes to a common pixel of the electronic views; and c) finally, summing the electronic views such that the pixels of each electronic view corresponding to the incremental element on the first selected focal plane are summed to generate a slice image taken through the first selected focal plane.

Known methods have the disadvantage that CT-scanning delivers cross-sectional images of the patient body whereas fluoroscopic X-ray images deliver two-dimensional images and, therefore, many X-ray images are required in several parallel planes and under several different angles of the radiation source to obtain a three-dimensional model.

The present invention provides a virtual three-dimensional representation of a bone or bone fragment, which representation may be based on two-dimensional images such as fluoroscopic images. Accordingly, the present invention may advantageously allow representations with reduced radiation exposure to the patient and less invasive surgical operations.

SUMMARY OF THE INVENTION

One aspect of the invention relates to a method for establishing a virtual three-dimensional (3-D) representation of a portion of a bone. It is understood that the portion of the bone may comprise the entire bone or merely a subset of the bone. For example, the portion of the bone may comprise a bone fragment, which may be separated from other portions of the bone by a break. The 3-D representation may be established from images, such as X-ray images. The images may be two-dimensional. The method may include obtaining at least one medical image of a patient's bone or bone fragment. The at least one medical image may be stored, for example as a data set in a data storage means of a computer.

The at least one medical image may be displayed, such as by using a display means, preferably operably connected to the computer. A 3-D virtual representation of the bone or bone fragment may be created by means of using a control means preferably connected to the computer. The size of the 3-D virtual representation may be adjusted to the size of the bone or bone fragment by means of using the control means. The virtual representation may have a lower symmetry than the bone or bone fragment. For example, in one embodiment, the virtual representation comprises a cylindrical portion having a central axis.

The virtual representation comprising the cylindrical portion may preferably be rotated about the central axis without changing the apparent orientation of the virtual representation. An image of a bone or bone fragment, in contrast, will generally not posses a central axis about which the image may be rotated without changing the apparent orientation of the bone or bone fragment.

A second medical image of a bone or bone fragment of the patient may be obtained. The second medical image may be obtained at an angle with respect to the at least one medical image. The second medical image may be stored, such as in a second set of data in the data storage means of the computer. The first and second medical images may be displayed. A 3-D virtual representation of the bone or bone fragment may be created such as by means of using a control means connected to the computer. The size of the 3-D virtual representation may be adjusted to the size of the bone or bone fragment by means of using the control means.

In one embodiment, the method comprises reconstructing an axis of the bone or bone fragment preferably at the display means by using a control means. The axis may be reconstructed by defining at least two respective points on at least one of the images represented on the display means. The method may comprise reconstructing an axis of the bone or bone fragment through an automatic axis identification.

The virtual representation may comprises a enveloping surface of a bone or bone fragment. The enveloping surface may be aligned to the axis.

The virtual representation may comprise a body representing a bone or bone fragment, which body may be aligned to the axis.

The method may comprise step of loading a set of image data of a surgical tool. The image data may be loaded into a processor of the computer. The surgical tool may be represented at the display means preferably together with the virtual representation of a respective bone or bone fragment. The virtual representation and/or the representation of the surgical tool may be displaced on the display means by using a control means connected to the computer.

The method may comprise loading a set of image data of a surgical implant into the processor of the computer. The surgical implant may be represented at the display means preferably together with the virtual representation of a respective bone or bone fragments. The virtual representation and the representation of the surgical implant may be displaced on the display means by using a control means.

The method may comprise rotating the virtual representation on the display means, such as by using a control means in order to receive a perspective view of the region of interest of a bone or bone fragments. A surgical action may be simulated at the display means such as by means of adjusting the virtual representation and arranging the surgical implant at its desired position.

The method may include attaching a reference means preferably at each bone or bone fragment. The position and orientation of each reference means may be measured, such as with respect to a system of coordinates by means of a position measurement device. The position and orientation of a further reference means fixedly attached to a mobile X-ray device having an axis of projection and a plane of projection may be measured. The position and orientation of said plane of projection with respect to the system of coordinates defined by the third reference means is preferably known.

The position and orientation of a fourth reference means fixedly attached to a surgical tool may be measured.

One embodiment of the invention relates to a method for preparing a virtual three-dimensional representation of a first portion of a bone, which may be the entire bone or a subset thereof. The method may include obtaining, from a first orientation with respect to the first portion of the bone, first image data of the first portion of the bone and obtaining, from a second, different orientation with respect to the first portion of the bone, second image data of the first portion of the bone. A three-dimensional (3D) virtual representation of the first portion of the bone may be generated. The 3D virtual representation of the first portion of the bone may be displayed. The displayed 3D virtual representation may have an orientation, which is preferably determined using at least the difference between the first and second orientations from which the first and second image data were obtained. At least one of the first and second images may be a two-dimensional image.

An image of the first portion of the bone may be displayed. The displayed 3D virtual representation of the first portion of the bone and the image of the first portion of the bone may be overlaid.

One embodiment of the invention relates to a method for preparing a virtual three-dimensional representation of a first portion of a bone. The method may comprise obtaining, from a first orientation with respect to the first portion of the bone, first two-dimensional image data of the first portion of the bone and obtaining, from a second, different orientation with respect to the first portion of the bone, second two-dimensional image data of the first portion of the bone. Preferably based on at least the first and second image data, a virtual representation of the first portion of the bone may be generated. The virtual representation preferably has a lower symmetry than the first portion of the bone. On a display device, an image of the virtual representation of the first portion of the bone and an image of the first portion of the bone may be overlaid. An orientation of the displayed virtual representation is preferably indicative of an intraoperative orientation of the first portion of the bone.

Another embodiment of the invention relates to a system configured to prepare a virtual three-dimensional representation of a first portion of a bone. The system may comprise a display device and a processor in communication with the display device. The processor is preferably configured to receive first two-dimensional image data of the first portion of the bone, the first two-dimensional image data having been obtained from a first orientation with respect to the first portion of the bone. The processor is preferably also configured to receive second two-dimensional image data of the first portion of the bone, the second two-dimensional image data having been obtained from a second, different orientation with respect to the first portion of the bone. The processor may be configured to generate, based on at least the first and second image data, a virtual representation of the first portion of the bone. The virtual representation preferably has a lower symmetry than the first portion of the bone. The processor may be configured to overlay, on the display device, (i) an image of the virtual representation of the first portion of the bone and (ii) an image of the first portion of the bone. An orientation of the displayed virtual representation is preferably indicative of an intraoperative orientation of the first portion of the bone.

BRIEF DESCRIPTION OF THE DRAWINGS

The present invention is discussed below in reference to the Drawings in which.

DETAILED DESCRIPTION OF THE PREFERRED EMBODIMENT

Figure 1:
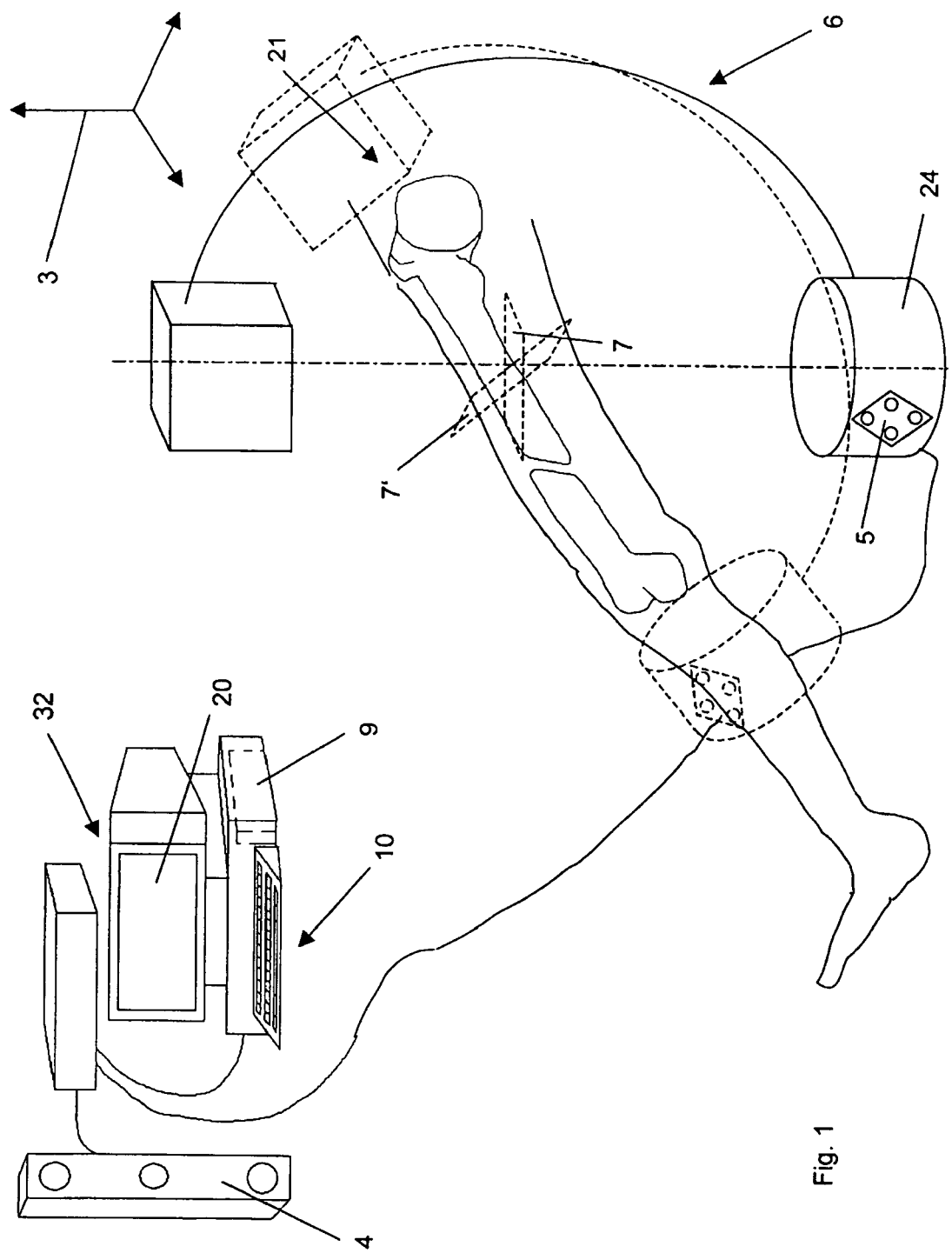
FIG. 1 schematically illustrates use of a C-arm X-ray device in communication with a computer in accordance with the present invention.

One aspect of the present invention relates to a method for establishing a virtual three-dimensional representation (3D model) from imaging data, such as X-ray images. At least some or all of the imaging data may be two-dimensional. In one embodiment, the method comprises positioning an imaging device, such as an X-ray device such that the region of interest at the patient's body may be mapped onto a plane of projection of the imaging device. The region of interest may be a portion of a patient's bone. At least one first medical image of the region of interest is mapped onto the plane of projection. The at least one first medical image may be stored as a set of image data in a data storage means of a computer. The image may comprise pixels, for example, a matrix of $128^2$ to $1024^2$ pixels.

The at least one first medical image may be displayed to a display means in communication with the computer. The display means may be a head mounted display. A three-dimensional virtual representation of the portion of the bone may be created by means of using a control means connected to the computer. The size of the three-dimensional virtual representation to the size of the portion of the bone by means of using the control means. The creation and adjustment of the virtual three-dimensional representation using the control means may be performed visually through using a keyboard or virtual keyboard, a mouse or a pointer as control means and determining the shape and dimensions visually at the display means.

The method may comprise taking a second medical image of the portion of the bone at a preferably non-zero angle with respect to the first medical image. The second medical image may be stored as a set of data in the data storage means of the computer. The first and second medical images may be displayed, such as simultaneously. A three-dimensional virtual representation of the portion of the bone may be created by means of using a control means connected to the computer. The size of the three-dimensional virtual representation may be adjusted to the size of the bone or bone fragment by means of using the control means.

The method may comprise reconstructing an axis, e.g., the central axis of the at least one portion of the bone. The axis may be reconstructed by defining respective points on the at least one medical image represented on the display means, e.g., the display of the computer. The definition of these points may be performed using, for example, with a keyboard or virtual keyboard, a mouse, a pointer, or other input device. Alternatively, the automatic axis may be identified by computer, such as by using automatic surface or volume methods (chamfer methods) and/or identification of anatomical points. The size of the virtual representation is preferably adjusted until the projection boundary size of the virtual representation is close to the projected image boundary.

The reconstruction of an axis of the portion of the bone that is to be represented through the respective virtual representation may be achieved by reconstructing two or more points on the specific axis. Each point is preferably reconstructed by choosing one or more projection points from each of at least two acquired images. Preferably, the computer is provided with an algorithm that allows the projection of the X-ray beam for each selected point on the other images through a thin line. This allows verification of the selected point and facilitates the identification of the other point that must be chosen on the displayed line.

The definition and adjustment of the virtual representation is preferably performed in a perspective representation determined from the projected images taken with a C-arm X-ray device. Preferably after the virtual representation is defined and adjusted to the images of the portion of the bone, a check may be performed whether the projected images of the bone or bone fragment are covered by the projected boundary of the virtual representation which is calculated through a specific C-arm X-ray projection model. The projected images preferably correspond to the images taken by the imaging device, e.g., the C-arm X-ray device. Since the virtual representation is defined from images of the portion of the bone that have a different axis of projection, a three-dimensional representation with a central axis coinciding with the longitudinal axis of the portion of the bone may be established. Therewith, a more precise manipulation of the portion of the bone is possible.

One embodiment of the invention comprises representing surgical tools and surgical implants at a display means connected to the computer together with virtual representations of respective portions of the bone. The virtual representations may preferably be displaced such as to allow planning a surgical action. A keyboard or virtual keyboard, a mouse, a pointer, or other input device may be used to displace the virtual bone representations, the surgical tools, and surgical implants on the display. Geometrical models of the surgical tools and implants that are provided by their manufacturers may be used.

The method according to the invention may be used as a planning method for a subsequent surgical action using computer assisted surgical navigation to perform the surgical action. The method may including attaching a reference means preferably at each portion of the bone involved in the surgical action. The position and orientation of each reference means may be measured with respect to a system of coordinates by means of a position measurement device. The position and orientation of a third reference means fixedly attached to a C-arm X-ray device having an axis of projection and whereof the position and orientation of the plane of projection may be measured with respect to the system of coordinates defined by the third reference means is known. The position and orientation of a fourth reference means fixedly attached to a surgical tool or implant may be measured.

Fluoroscopy based systems allow superimposed real-time virtual line graphics visualization of the projection of surgical tools and bone portions relative to the acquired C-arm X-ray images. Therefore, a comprehensive calibration procedure is preferably applied where all physical parameters are determined that specify imaging attributes. These parameters may then recalled and combined with an imaging device's current spatial position and orientation with respect to the patient's anatomy. Advantageously, the pre-calibration of the C-arm X-ray device may be performed in three steps: extrinsic, intrinsic and mechanic calibration. Extrinsic calibration preferably provides external geometric parameters describing the X-ray projection such as the initial focal point (X-ray emitter) and image plane positions. Intrinsic calibration preferably extracts parameters quantifying the distortions caused by the electronic optics of the image intensifier. It allows a correction for these distortions in every acquired image. As most C-arm X-ray devices are subject to significant elastic frame deformations when their position is changed, a mechanic calibration compensates the related variations of the focal point. The deformations of the C-arm X-ray device may be mapped over the whole range of motion of the imaging device to be able to interpolate between these values.

The reference means preferably comprise at least three markers that are non-collinearly arranged. The markers as well as the detectors of the position measurement device may be acoustic or electromagnetic effective means such as energy emitting, receiving or reflecting means. For example, light sources, particularly light emitting diodes (LED's), which include infrared light emitting diodes (IRED's), or acoustic transmitters may be used. Exemplary energy receiving means include detectors such as photodiodes and microphones. Other suitable position measurement devices comprise coils as energy emitting means. Hall-effect components may be used as energy receiving means.

Each reference means preferably defines a local system of coordinates with a fixed mathematical relation to every point of the body e.g., the bone portion, surgical tool or surgical implant where the reference means is attached to. The position measurement device is preferably in communication with a computer. By means of the position measurement device coordinate transformations between any of the above systems of coordinates may be performed. A medical image taken by means of the C-arm X-ray device reflects to momentary position of the bone portion and must therefore be registered to each reference means attached at the bone portion. For example, matrices providing coordinate transformations between the system of coordinates of the reference means at the C-arm X-ray device and the reference means attached at the bone portion may be obtained by measuring the positions and orientations by means of the position measurement device and then stored at the acquisition time of the respective image in the data storage means of the computer.

An exemplary optoelectronic position measurement device is the OPTOTRAK 3020 System, available from Northern Digital of Waterloo, Ontario, Canada. Optoelectronic position measurement devices in accordance with the invention preferably comprise a position sensor, such as one comprising three one-dimensional light detectors, such as charge-coupled devices (CCD) paired with three lens cells and mounted on a stabilized bar. The light detectors detect light from markers of reference frames. Preferably, measurements from three or more detectors are used to determine the three-dimensional location of the marker. The position measurement device may include a system control unit, a computer interface card and cables, data collection and display software, and a strober and marker kit.

In accordance with the invention, a three-dimensional representation of a bone or bone fragment may be established from two-dimensional C-arm X-ray images. The higher dimensionality of the 3-D representation allows a higher precision when manipulating the bone or bone fragment during the surgical action than the present use of two-dimensional images produced by the C-arm X-ray device. Furthermore, the necessary amount of fluoroscopic images to be taken of the patient's body and therewith the time of exposure to radiation may be significantly reduced. The present invention allows optimal selection of the shape of surgical implants that shall be implanted into the patient's body by means of the planned surgical action e.g., size and length of an intramedullary nail, bending of a plate or position of screws.

Referring to FIG. 1, the positioning an imaging device, which in this Figure is a mobile X-ray device 6 (C-arm X-ray device), in different positions with respect to a bone 21 is shown. Positioning the imaging device 6 in different positions with respect to the bone 21 allows a region of interest of the bone 21 to be mapped from different angles of view on the plane of projection 7 of the X-ray device 6. Preferably, a first and a second image 11;13 are obtained. The first and second images may be saved as first and second data sets of data to a storage medium 9 of a computer 10.

Figure 2:
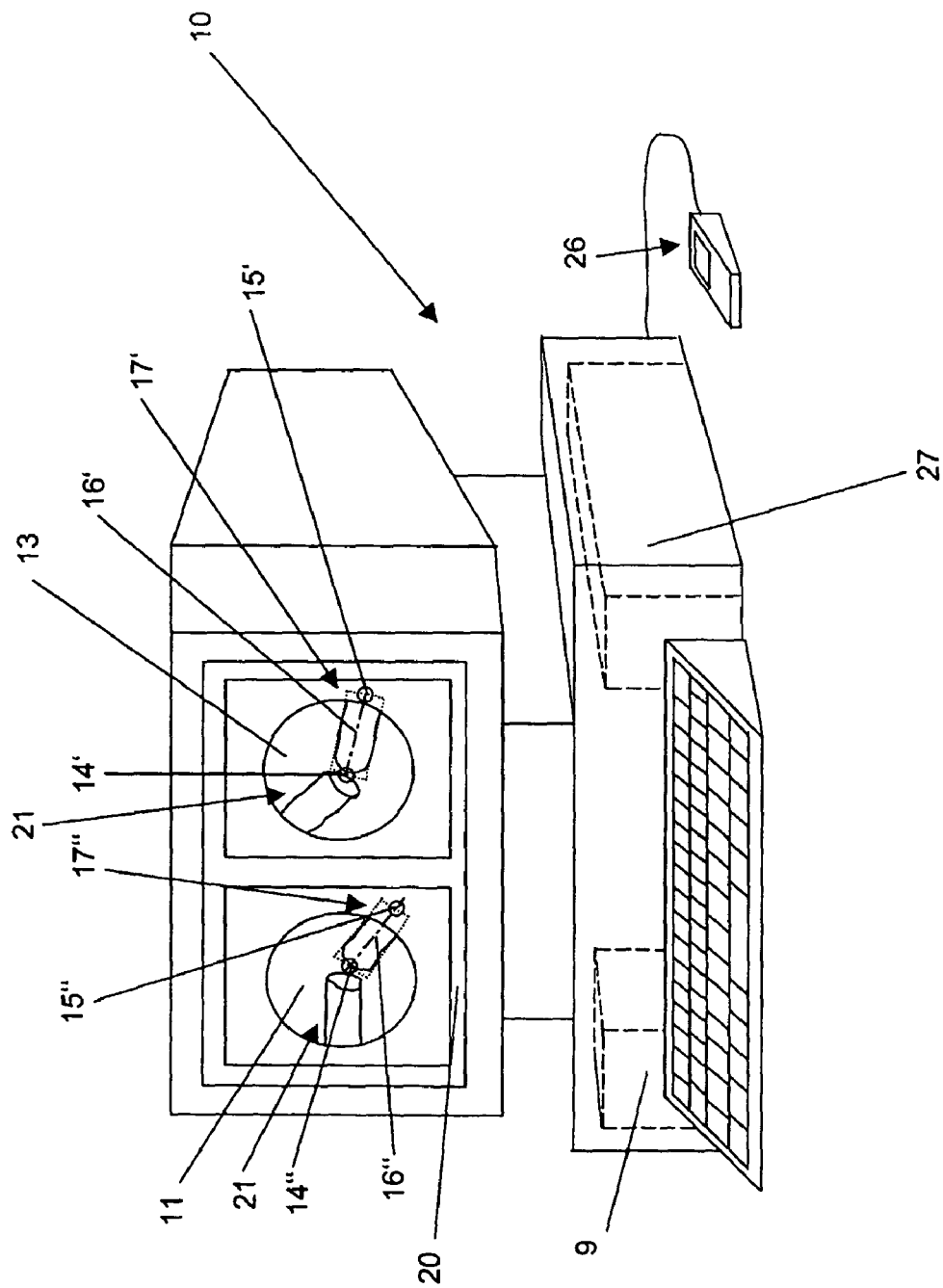
FIG. 2 illustrates an embodiment of establishing a virtual three-dimensional representation using a computer in accordance with the present invention.

Referring to FIG. 2, the images 11;13 may be displayed at a display 32 which is preferably in communication with the computer 10. Other display means such as a head mounted display may be used as well.

Figure 3:
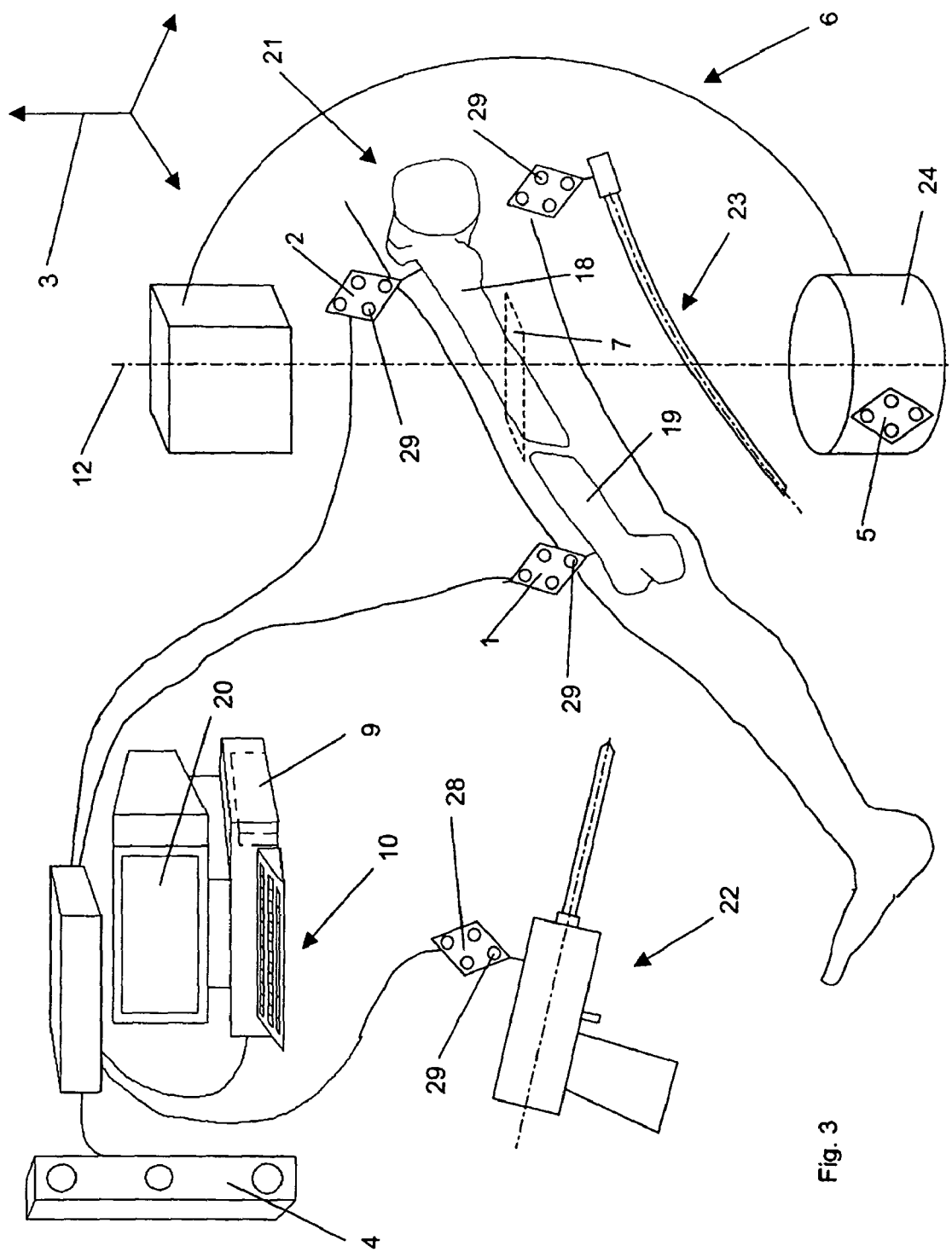
FIG. 3 illustrates reduction of a fractured bone in accordance with the present invention.

Referring to FIG. 3, a position measurement device 4 may be used to determine the position of markers 29 having a known spatial relationship with the imaging device 6. Based upon the position of the markers 29 and the known spatial relationship with the imaging device 6, the position and orientation of the plane of projection 7,7' for each position of the X-ray device 6 may be determined with respect to an on-site system of coordinates 3. It should be understood that determination of the position of the imaging device 6 is not essential to the invention. In one embodiment, for example, the virtual representation may comprise a symmetrical representation, e.g. a virtual cylinder coaxial to the specified axis 16', 16" of the bone 21.

Generating of a virtual representation in accordance with the invention may comprise identifying a longitudinal axis of at least a portion of a bone. Preferably, a display of the virtual representation of the bone extends along the longitudinal axis. FIG. 2 depicts an example of generating a virtual representation in two images 11;13 of a fractured bone 21. The bone 21 may comprise first and second portions separated by a break. Image 11 is taken at an anterior-posterior view and the image 13 is taken at a lateral-medial view of a region of interest of the bone 21. Using an input device, such as a mouse 26, a first point 14' and a second point 15' may be selected in image 11. A first point 14" and a second point 15" may be selected in image 13. Points 14' and 15' may be used to specify a first longitudinal axis 16' of the bone 21. Points 14" and 15" may be used to specify a second longitudinal axis 16' of the bone 21.

Preferably by using one or both of axes 16' and 16" of the bone 21, a virtual representation of the bone may be determined. FIG. 2 shows an anterior-posterior projection 17" of a virtual representation 17 within first image 11 and a lateral-medial projection 17' of virtual representation 17 within second image 13. Using input device 26, the size of the virtual representation 17 may be adjusted with respect to the size of the bone 21, such as by adjusting one or both of the projected virtual cylinders 17';17" to the displayed bone 21.

Virtual representation 17 comprises a cylindrical central portion and may preferably be rotated about a central axis of the cylindrical central portion without changing the apparent orientation of the virtual representation with respect to the bone.

FIG. 3 illustrates a computer assisted closed reduction of a fractured bone 21 in accordance with the invention. Preferably but not necessarily after a virtual representation of the proximal and distal bone fragments 18;19 is established and displayed, e.g., using the display 20 of the computer 10, a set of image data of a surgical tool 22 is provided to computer 10. The surgical tool may comprise, for example, a drill drive. A reference means 28 is preferably secured to the surgical tool 22. The relative position of the surgical instrument 22 may be determined with respect to the first and second reference means 1;2, such as by determining the position of the markers 29 on each of the reference means 1, 2, and 28 with respect to the three-dimensional system of coordinates 3. The positions may be determined using the position measurement device 4.

Figure 4:
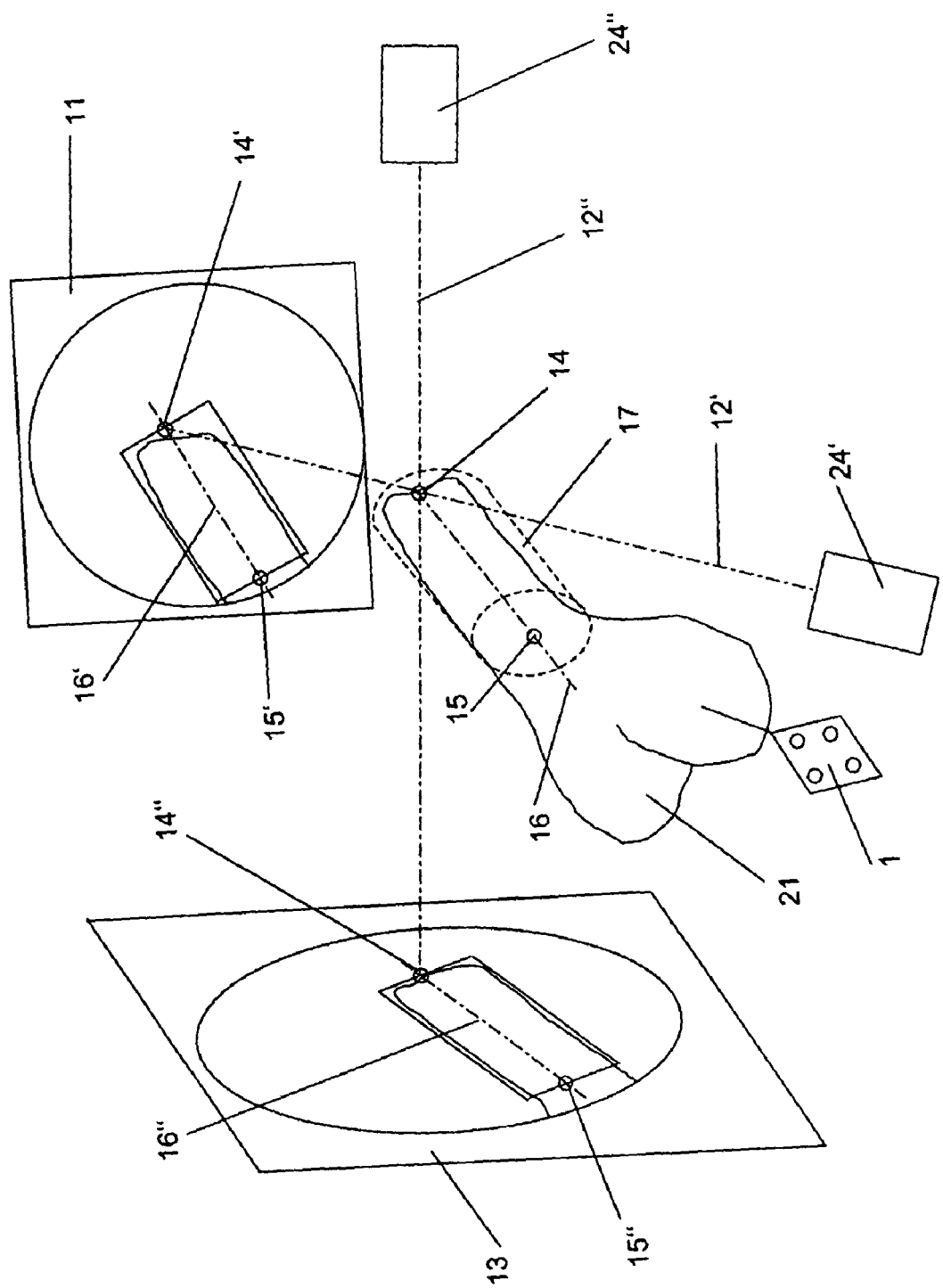
FIG. 4 illustrates adjustment of a virtual three-dimensional representation to a bone or bone fragment in accordance with the present invention.

Referring to FIG. 4, an operator may register the images 11;13 taken by the imaging device 6. For example, the operator may manually identify an anatomical landmark of at the bone fragment 18;19 on the two images 11;13 represented at a display. The three-dimensional position of the anatomical landmark relative to the corresponding reference base 1; 2 may be determined, such as through coordinate transformations between the system of coordinates affixed to the images, the system of coordinates affixed to the plane of projection 7, the system of coordinates affixed to the third reference means 5 attached at the X-ray device 6 and the on-site system of coordinates 3.

Virtual representations in accordance with the invention may be used to intraoperatively visualize the position of the virtual representation directly and based on the measured positions of the bone fragments 18;19. The operator may perform the alignment of the bone fragments 18;19 with direct visual control. As the surgeon displaces the bone fragment 18;19, the corresponding virtual representation may be moved as well on the display 20. Similarly, a surgical tool 22 or surgical implant 23, e.g. an intramedullary nail may be intraoperatively guided with direct visual control at the display 20.

While the above invention has been described with reference to certain preferred embodiments, it should be kept in mind that the scope of the present invention is not limited to these. Thus, one skilled in the art may find variations of these preferred embodiments which, nevertheless, fall within the spirit of the present invention, whose scope is defined by the claims set forth below.

What is claimed is:

1. A method for preparing a virtual three-dimensional representation of a first portion of a bone comprising the steps of:
   obtaining, from a first orientation with respect to the first portion of the bone, first image data of the first portion of the bone;
   obtaining, from a second, different orientation with respect to the first portion of the bone, second image data of the first portion of the bone;
   generating a three-dimensional (3D) virtual representation of the first portion of the bone; and
   displaying the 3D virtual representation of the first portion of the bone, the displayed 3D virtual representation having an orientation, the orientation of the displayed 3D virtual representation being determined using at least the difference between the first and second orientations from which the first and second image data were obtained,
   wherein the displayed 3D virtual representation has a lower symmetry than the first portion of the bone.

2. The method of claim 1, wherein at least one of the first and second images is a two-dimensional image.

3. The method of claim 2, wherein both the first and second images are two-dimensional images.

4. The method of claim 3, wherein at least one of the first and second images is a fluoroscope image.

5. The method of claim 1, comprising: displaying an image of the first portion of the bone; and overlaying the displayed 3D virtual representation of the first portion of the bone and the image of the first portion of the bone.

6. The method of claim 5, wherein the displayed image of the first portion of the bone comprises at least some data from at least one of the first and second image data.

7. The method of claim 5, comprising: determining an intraoperative orientation of the bone; and wherein the orientation of the displayed 3D virtual representation of the first portion of the bone is indicative of the intraoperative orientation of the first portion of the bone.

8. The method of claim 5, wherein the step of determining the intraoperative position of the first portion of the bone comprises: securing at least one of (a) a set of energy emitters or (b) a set of energy detectors to the first portion of the bone; and detecting, using the set of energy detectors, energy emitted by the energy emitters of the set of energy emitters.

9. The method of claim 8, wherein, if the intraoperative orientation of the first portion of the bone changes, updating the orientation of the displayed 3D virtual representation of the first portion of the bone so that the orientation of the displayed 3D virtual representation remains indicative of the intraoperative orientation of the first portion of the bone.

10. The method of claim 5, comprising using an input device to adjust a dimension of the 3D virtual representation to correspond with a dimension of the first portion of the bone.

11. The method of claim 7, wherein the dimension of the first portion of the bone is a diameter.

12. The method of claim 7, wherein the dimension of the first portion of the bone is a length.

13. The method of claim 1, wherein the displayed 3D virtual representation comprises a cylindrical portion.

14. The method of claim 1, comprising the steps of: obtaining, from a third orientation with respect to a second portion of the bone, third image data of the second portion of the bone; obtaining, from a fourth, different orientation with respect to the second portion of the bone, fourth image data of the first portion of the bone; generating a three-dimensional (3D) virtual representation of the second portion of the bone; and displaying the 3D virtual representation of the second portion of the bone, the displayed 3D virtual representation of the second portion of the bone having an orientation, the orientation of the displayed 3D virtual representation of the second portion of the bone being determined using the difference between the third and fourth orientations from which the third and fourth image data were obtained.

15. The method of claim 14, wherein the first and second orientations are the same as, respectively, the third and fourth orientations.

16. The method of claim 14, comprising: displaying an image of the second portion of the bone, the displayed image of the second portion of the bone comprising at least some data from at least one of the third and fourth image data; and overlaying the displayed 3D virtual representation of the second portion of the bone and the image of the second portion of the bone.

17. The method of claim 16, comprising using an input device to adjust a dimension of the 3D virtual representation of the second portion of the bone to correspond with a dimension of the second portion of the bone.

18. The method of claim 17, wherein the dimension of the second portion of the bone is a diameter.

19. The method of claim 16, comprising: determining an intraoperative orientation of the second portion of the bone; and wherein the orientation of the displayed 3D virtual representation of the second portion of the bone is indicative of the intraoperative orientation of the second portion of the bone.

20. The method of claim 19, wherein the step of determining the intraoperative position of the second portion of the bone comprises: securing at least one of (a) a set of energy emitters or (b) a set of energy detectors to the first portion of the bone; detecting, using the set of energy detectors, energy emitted by the energy emitters of the set of energy emitters.

21. The method of claim 20, wherein, if the intraoperative orientation of the second portion of the bone changes, updating the orientation of the displayed 3D virtual representation of the second portion of the bone so that the orientation of the displayed 3D virtual representation of the second portion of the bone remains indicative of the intraoperative orientation of the second portion of the bone.

22. The method of claim 19, wherein the first portion and second portion of the bone are separated by a break and the method further comprises: manipulating at least one of the first and second portions of the bone with respect to the other; and observing the respective virtual representations of the first and second bones.

23. The method of claim 17, wherein the dimension of the second portion of the bone is a length.

24. The method of claim 1, wherein the displayed 3D virtual representation of the second portion of the bone has a lower symmetry than the second portion of the bone.

25. The method of claim 24, wherein the displayed 3D virtual representation of the second portion of the bone comprises a cylindrical portion.

26. A method for preparing a virtual three-dimensional representation of a first portion of a bone comprising the steps of:
obtaining, from a first orientation with respect to the first portion of the bone, first two-dimensional image data of the first portion of the bone;
obtaining, from a second, different orientation with respect to the first portion of the bone, second two-dimensional image data of the first portion of the bone;
generating, based on at least the first and second image data, a virtual representation of the first portion of the bone, the virtual representation having a lower symmetry than the first portion of the bone; and
overlaying, on a display device, (i) an image of the virtual representation of the first portion of the bone and (ii) an image of the first portion of the bone, wherein an orientation of the displayed virtual representation is indicative of an intraoperative orientation of the first portion of the bone.

27. The method of claim 26, comprising: obtaining, from a third orientation with respect to a second portion of the bone, third two-dimensional image data of the second portion of the bone; obtaining, from a third, different orientation with respect to the first portion of the bone, fourth two-dimensional image data of the second portion of the bone; generating, based on at least the second and fourth image data, a virtual representation of the second portion of the bone, the virtual representation of the second portion of the bone having a lower symmetry than the second portion of the bone; and overlaying, on a display device, (i) an image of the virtual representation of the second portion of the bone and (ii) an image of the second portion of the bone, wherein an orientation of the displayed virtual representation of the second portion of the bone is indicative of an intraoperative orientation of the second portion of the bone.

28. The method of claim 27, wherein the first and second orientations are the same as, respectively, the third and fourth orientations.

29. The method of claim 26, wherein the step of generating comprises identifying a longitudinal axis of the displayed image of the first portion of the bone and wherein the image of the virtual representation of the first portion of the bone extends along the longitudinal axis of the displayed image of the first portion of the bone.

30. A system configured to prepare a virtual three-dimensional representation of a first portion of a bone, the system comprising:
a display device; and
a processor in communication with the display device, the processor configured to:
receive first two-dimensional image data of the first portion of the bone, the first two-dimensional image data having been obtained from a first orientation with respect to the first portion of the bone;
receive second two-dimensional image data of the first portion of the bone, the second two-dimensional image data having been obtained from a second, different orientation with respect to the first portion of the bone;
generate, based on at least the first and second image data, a virtual representation of the first portion of the bone, the virtual representation having a lower symmetry than the first portion of the bone; and
overlay, on the display device, (i) an image of the virtual representation of the first portion of the bone and (ii) an image of the first portion of the bone, wherein an orientation of the displayed virtual representation is indicative of an intraoperative orientation of the first portion of the bone.

* * * * *

UNITED STATES PATENT AND TRADEMARK OFFICE
CERTIFICATE OF CORRECTION

PATENT NO. : 7,117,027 B2
APPLICATION NO. : 10/629589
DATED : October 3, 2006
INVENTOR(S) : Zheng et al.

It is certified that error appears in the above-identified patent and that said Letters Patent is hereby corrected as shown below:

On the title page, at Item (75):

Please replace "Lutz-Peter Nolte, Thun (CN)" with -- Lutz-Peter Nolte, Thun (DE) --.

Signed and Sealed this

Tenth Day of April, 2007

JON W. DUDAS
*Director of the United States Patent and Trademark Office*